US00PP32193P3

(12) United States Plant Patent
Leis et al.

(10) Patent No.: US PP32,193 P3
(45) Date of Patent: Sep. 15, 2020

(54) STRAWBERRY PLANT NAMED 'CIVRL333'

(50) Latin Name: ***Fragaria* x *ananassa***
Varietal Denomination: CIVRL333

(71) Applicant: C.I.V.—CONSORZIO ITALIANO VIVAISTI—SOCIETÀ CONSORTILE A R.L., Comacchio FE (IT)

(72) Inventors: Michelangelo Leis, Ferrara (IT); Alessio Martinelli, Ferrara (IT)

(73) Assignee: C.I.V.—CONSORZIO ITALIANO VIVAISTI—SOCIETA CONSORTILE A R.L., Comacchio (IT)

( * ) Notice: Subject to any disclaimer, the term of this patent is extended or adjusted under 35 U.S.C. 154(b) by 0 days.

(21) Appl. No.: 16/602,446

(22) Filed: Oct. 8, 2019

(65) Prior Publication Data

US 2020/0187403 P1 Jun. 11, 2020

(30) Foreign Application Priority Data

Dec. 10, 2018 (QZ) ..... PBR 2018/3270

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 5/08; A01H 6/74
See application file for complete search history.

*Primary Examiner* — Annette H Para
(74) *Attorney, Agent, or Firm* — Foley & Lardner LLP

(57) ABSTRACT

This invention relates to a new and distinct variety of strawberry plant named 'CIVRL333'. This new strawberry plant named 'CIVRL333' is primarily adapted to the climate and growing conditions of the low chill areas but it is also adapted for Northern European countries, Mediterranean and Subtropical areas. It is characterized by a plant with good vigor, upright habit and an excellent tolerance to most common diseases. The fruit is attractive with bright red color, regular shape and big size for the entire picking season and a very resistant skin even at high temperatures. The flesh is juicy, with sweet flavor and lovely aroma. The fruit is unique among the everbearer low chill varieties. Very early and long lasting picking season.

4 Drawing Sheets

Figure 1:
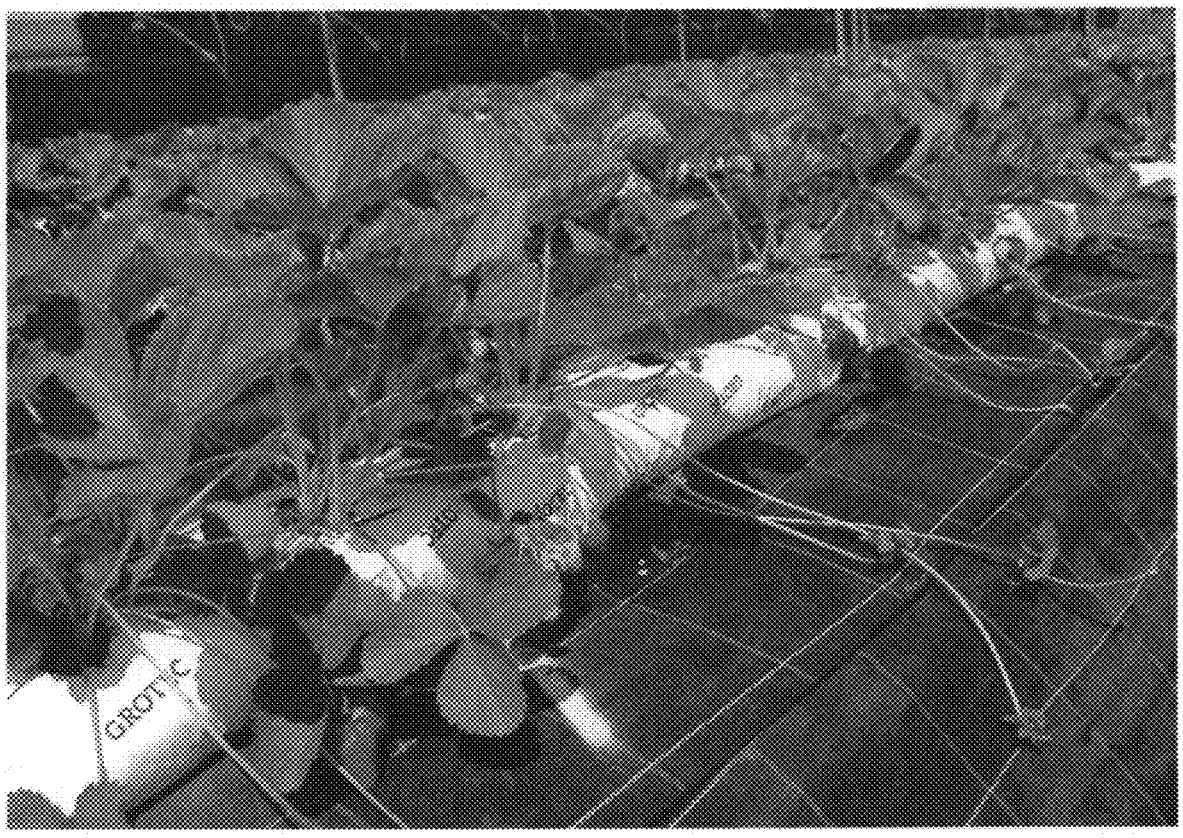

Latin name of the genus and species of the plant claimed: *Fragaria* x *ananassa.*

Variety denomination: 'CIVRL333'.

BACKGROUND OF THE INVENTION

The present invention relates to a new and distinct strawberry variety named 'CIVRL333'.

The new strawberry 'CIVRL333' is a product of a planned breeding program conducted by the inventors, Leis Michelangelo and Martinelli Alessio, in San Giuseppe di Comacchio (Ferrara), Italy. The objective of the breeding program is to develop a new everbearer strawberry variety with low chill requirement, wide climatic adaptability and excellent tolerance to most common diseases. Furthermore, they wanted to get a new everbearer low chill variety with very sweet flavor and lovely aroma. Lastly, the variety must be very early-season and lasting picking time.

This new strawberry 'CIVRL333' is a result of a controlled cross made by the inventors in 2011, in San Giuseppe di Comacchio (Ferrara), Italy. The female or seed parent is the not released selection of Consorzio Italiano Vivaisti named R6R11-26. The male or pollen parent is the not released selection of Consorzio Italiano Vivaisti named 3E4L-1.

The new strawberry 'CIVRL333' was discovered and selected by the inventors as a single flowering plant within the progeny of the stated cross in 2013 in San Giuseppe di Comacchio (Ferrara), Italy. After its selection, the new variety was asexually propagated by stolons in a nursery located in San Giuseppe di Comacchio (Ferrara), Italy. The new variety was tested over the next several years at Consorzio Italiano Vivaisti in San Giuseppe di Comacchio (Ferrara), Italy and in different European areas with low chill conditions and high chill condition. This propagation has demonstrated that the combination of characteristics as herein disclosed for the new cultivar are firmly fixed and retained through successive generations of asexual reproduction. The new cultivar reproduces true to type.

BRIEF SUMMARY OF THE INVENTION

'CIVRL333' is an everbearer strawberry variety with low chill requirement but it has a wide climatic adaptability, from Northern European countries to Mediterranean and Subtropical areas.

The following traits have been repeatedly observed and are determined to be unique characteristics of 'CIVRL333', which in combination distinguish this strawberry plant as a new and distinct variety:

1. everbearer variety with low chill requirement;
2. wide climatic adaptability;
3. excellent tolerance to most common disease;
4. fruits with regular shape and big size for all the picking season;
5. very resistant fruit skin;

6. bright red color of the fruits;
7. fruit with very sweet flavor, with lovely aroma, unique of king among the everbearer low chill varieties; and
8. very early picking season and long lasting.

Of the many commercial cultivars known to the present inventor, the most similar in comparison to the new strawberry variety 'CIVRL333' is the patented strawberry variety Zafir property of Consorzio Italiano Vivaisti. Plants of the new strawberry variety 'CIVRL333' differ from plants of strawberry variety Zafir in the characteristics described in Table 2:

TABLE 2

| Characteristic | 'CIVRL333' | 'ZAFIR' |
|---|---|---|
| Plant: grow habit | Upright | Semi-upright |
| Fruit: color | Orange-red | Medium red |
| Type of bearing | Day neutral | Fully remontant |

BRIEF DESCRIPTIONS OF THE PHOTOGRAPHS

The accompanying color photographs illustrate the overall appearance of typical specimens of the new strawberry variety 'CIVRL333', at various stages of development as true as it is reasonably possible with color reproductions of this type. Color in the photographs may differ slightly from the color value cited in the botanical description which accurately describe the color of 'CIVRL333'. The depicted plant and plant parts of the new strawberry variety 'CIVRL333' were taken in San Giuseppe di Comacchio (Ferrara), Italy, and are approximately 3 to 5 months old.

Figure 2:
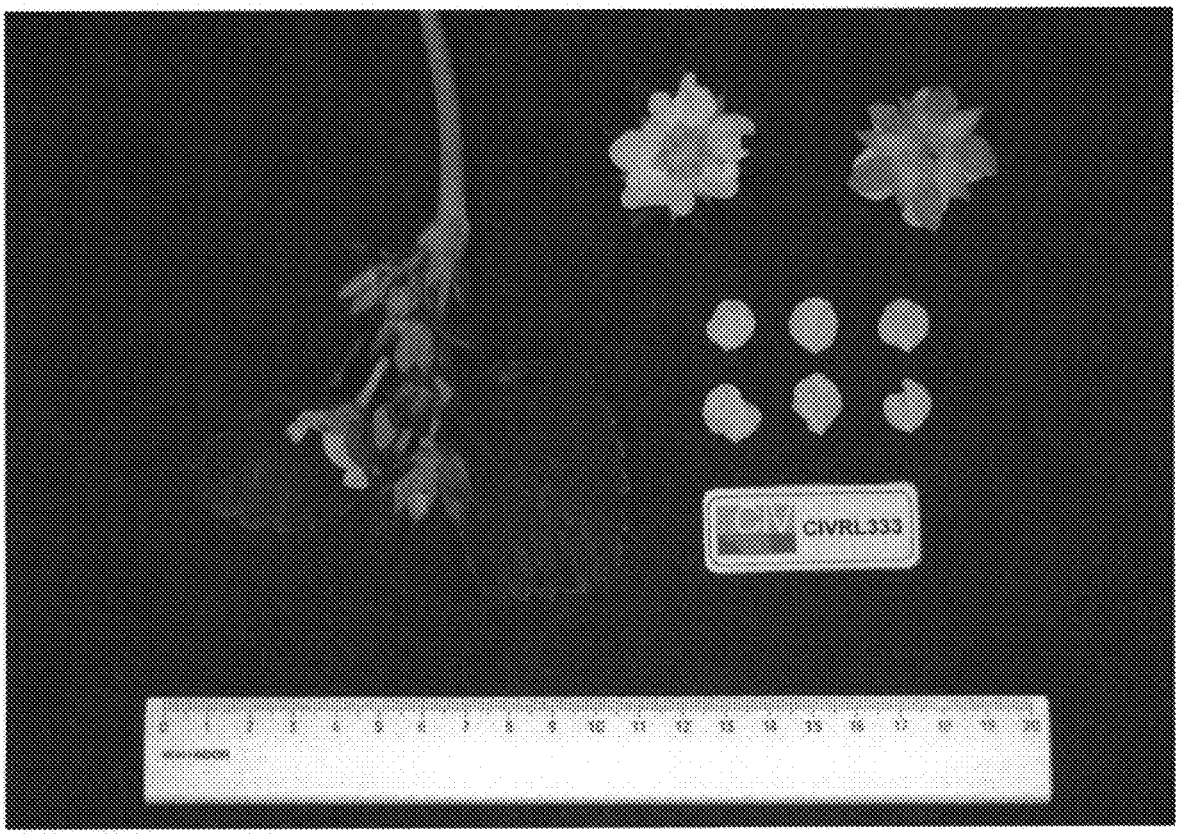
Figure 3:
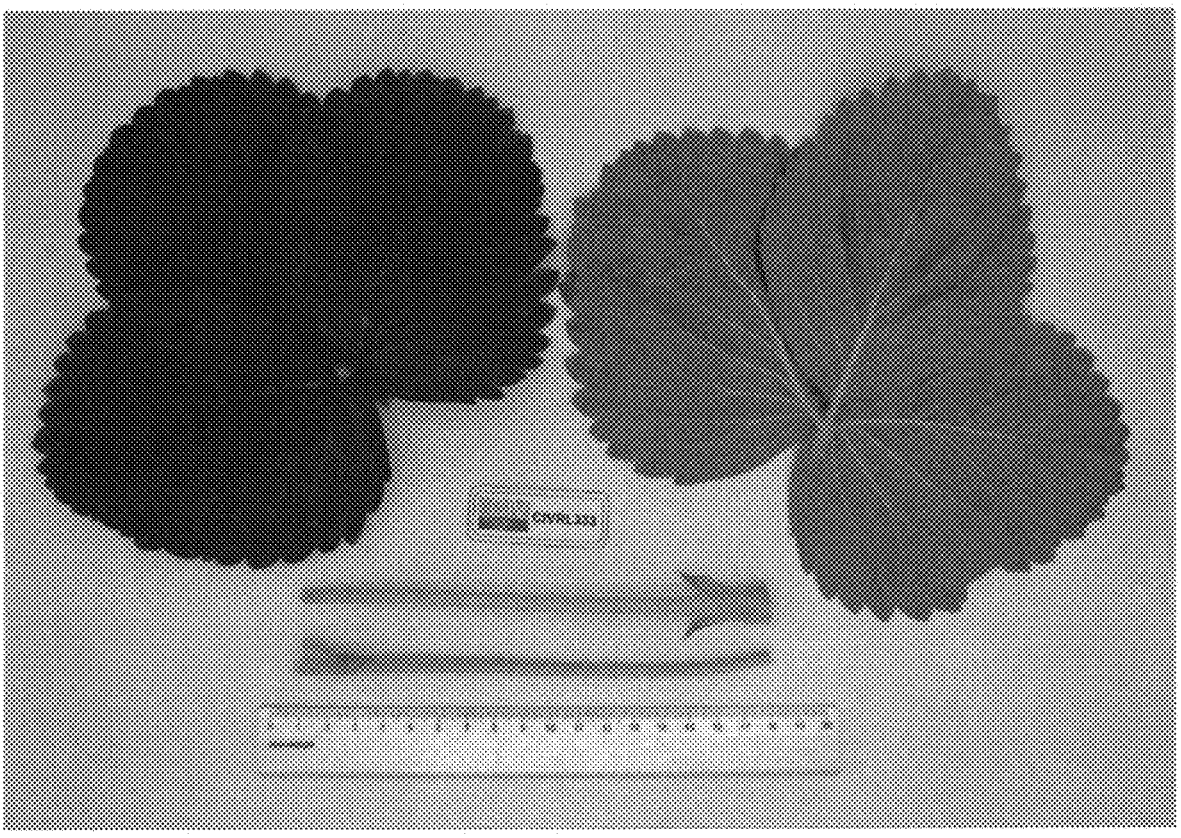
Figure 4:
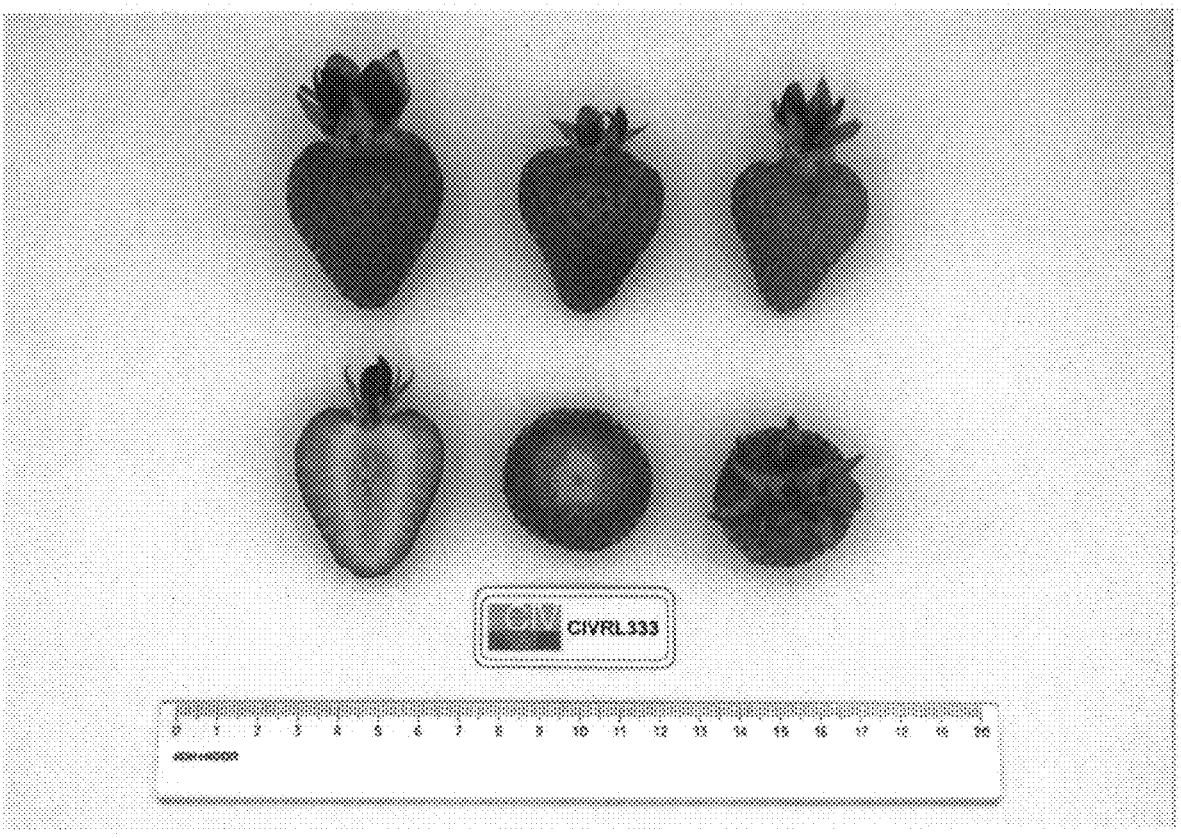

FIG. 1 shows typical plants of 'CIVRL333';
FIG. 2 shows typical flowers of 'CIVRL333';
FIG. 3 shows typical leaves of 'CIVRL333';
FIG. 4 shows typical fruits of 'CIVRL333'.

DETAILED BOTANICAL DESCRIPTION

'CIVRL333' has not been observed under all possible environmental conditions. The characteristics of the new variety may vary in detail, depending upon variations in environmental factors, including weather (temperature, humidity and light intensity), day length, soil type and location.

The aforementioned photographs, together with the following observations, measurements and values describe the new strawberry variety 'CIVRL333', unless otherwise noted, taken during the 2018 growing season in San Giuseppe di Comacchio (Ferrara), Italy. The observations, measurements and values were taken from plants of 'CIVRL333' dug from a low-elevation nursery located in San Giuseppe di Comacchio (Ferrara), Italy, during 2018 and planted approximately 4 months later in San Giuseppe di Comacchio (Ferrara), Italy. Plants of the new strawberry variety 'CIVRL333' were grown under conditions which closely approximate those generally used in commercial practice.

Yield observations and fruit quality characteristics are averaged from 2 years of data collected from the 2017 through 2018 growing seasons. Flower measurements and characteristics are from secondary flowers unless otherwise noted. Fruit characteristics and measurements are from secondary fruit unless otherwise noted.

Color references are made to The Royal Horticultural Society Colour Chart (R.H.S.), 2001 edition, except where general colors of ordinary significance are used. Color values were taken under daylight conditions at approximately 10:00 in San Giuseppe di Comacchio (Ferrara), Italy. The approximate age of the observed plants is 3 to 5 months.

The following tables 3-9 describe fruit, plant, stolon, foliage, fruiting truss, flower and pest/disease characteristics of the new strawberry 'CIVRL333'.

TABLE 3

FRUIT CHARACTERISTICS

| Characteristic | 'CIVRL333' |
|---|---|
| Color of mature fruit | Red (45A red group) |
| Color of internal flesh | Red (34B orange-red group) |
| Length (cm) | Average 4.4 cm |
| Width (cm) | Average 3.9 cm |
| Ratio length/width | 1.12 |
| Calyx diameter (cm) | Average 4.7 cm |
| Average weight (gm) | Average 18.4 gm |
| Achene color | Yellow (154B yellow-green group) |
| Number of achenes per $cm^2$ | About 6.3 achenes/$cm^2$ |
| Marketable yield (gm/pit) | Average 700-800 gm/plt |
| Size | Large |
| Predominant shape | Conical |
| Difference in shapes between primary and secondary fruit | None or very slight |
| Band without achenes | Absent or very narrow |
| Unevenness of surface | Even or very slight uneven |
| Evenness of color | Even or very slightly uneven |
| Glossiness | Medium |
| Insertion of achenes | Below the surface |
| Insertion of calyx | Level with fruit |
| Attitude of the calyx | Upwards |
| Size of calyx in relation to fruit diameter | Same size |
| Adherence of calyx | Very strong |
| Firmness of skin | Firm |
| Firmness of flesh | Firm |
| Distribution of red color of the flesh | Marginal and central |
| Hollow center expression | Absent or weak |
| Flavor | Very sweet with lovely aroma |
| Soluble solids (% brix) | 8.8° Brix |
| Time of first flowering | Early |
| Time of first harvesting | Early (first picking the $20^{th}$ of May, 2019 in San Giuseppe di Comacchio (Ferrara), Italy) |
| Harvest period | From the end of May to October |
| Type of bearing | Day neutral |

TABLE 4

PLANT CHARACTERISTICS

| Characteristic | 'CIVRL333' |
|---|---|
| Height (cm) | Average 28 cm |
| Spread (cm) | Average 35 cm |
| Size | Medium |
| Habit | Upright |
| Density | Medium |
| Vigor | Strong |

TABLE 5

| STOLON CHARACTERISTICS | |
|---|---|
| Characteristic | 'CIVRL333' |
| Average number per plant | About 30 stolons/mother plant in our nursery in San Giuseppe di Comacchio (Ferrara) Italy |
| Anthocyanin coloration | Red (178 B greyed-red group) |
| Anthocyanin intensity | Strong. The anthocyanin coloration is present along all the stolon. |
| Diameter at bract (mm) | Average 2.5 mm |
| Pubescence | Dense |

TABLE 6

| FOLIAGE CHARACTERISTICS | |
|---|---|
| Characteristic | 'CIVRL333' |
| Foliage: | |
| Color of upper surface | Green (137A green group) |
| Color of underside | Green (138B green group) |
| Shape in cross section | Concave |
| Interveinal blistering | Medium |
| Glossiness | Weak |
| Number of leaflets | Three (3). |
| Terminal Leaflet: | |
| Length (cm) | Average 12.7 cm |
| Width (cm) | Average 11.3 cm |
| Length/width ratio | 1.12 |
| Serrations/leaf | Intermediate |
| Size | Big |
| Shape of base | Acute |
| Shape of teeth | Serrate to crenate |
| Petiole: | |
| Length (cm) | Average 17 cm |
| Diameter (mm) | Average 4.9 mm |
| Petiolule length (mm) | Average 6.7 mm |
| Pubescence | High |
| Attitude of hairs | Upright |
| Stipule: | |
| Length (mm) | Average 28.6 mm |
| Width (mm) | Average 8.8 mm |
| Anthocyanin coloration | Low |
| Color | Red (63 A red-purple group) |

TABLE 7

| Characteristic | 'CIVRL333' |
|---|---|
| Length (cm) | Average 27 cm |
| Position relative to foliage | Level with foliage |

TABLE 7-continued

| Characteristic | 'CIVRL333' |
|---|---|
| Pubescence | Strong |
| Anthocyanin coloration | Absent |
| Attitude at first pick | Outwards |

TABLE 8

| FLOWER CHARACTERISTICS | |
|---|---|
| Characteristic | 'CIVRL333' |
| Petal color | |
| Mature (upper) | White (155 D white group) |
| Mature (lower) | White (155 D white group) |
| Petal shape | |
| Overall | Rounded |
| Apex | Round |
| Base | Broad |
| Petal length (mm) | Average 11.8 mm |
| Petal width (mm) | Average 12 mm |
| Petal length/width ratio | 0.98 |
| Number of petals/flower | About 5 to 7 |
| Sepals color | |
| Mature (upper) | Green (141 A green group) |
| Mature (lower) | Green (138 A green group) |
| Sepal shape | |
| Overall | Elliptic |
| Apex | Pointed |
| Base | Narrow to broad |
| Sepal length (mm) | Average 14.3 mm |
| Sepal width (mm) | Average 6.6 mm |
| Sepal length/width ratio | 2.2 |
| Number of sepals/flower | About 12 |
| Corolla diameter (mm) | Average 31.5 mm |
| Calyx diameter (mm) | Average 39 mm |
| Size of calyx relative to corolla | Large |
| Relative position of petals | Touching |

TABLE 9

| PEST AND DISEASE REACTIONS |
|---|
| 'CIVRL333' shows excellent tolerance to most common diseases. |

We claim:

1. A new and distinct strawberry plant named 'CIVRL333', as herein described and illustrated by the characteristics set forth above.

* * * * *